United States Patent
Ristas (10) Patent No.: US 11,247,099 B2
(45) Date of Patent: Feb. 15, 2022

(54) PROGRAMMED CONTROL OF ATHLETIC TRAINING DRILLS

(71) Applicant: Lombro James Ristas, Windsor, CT (US)

(72) Inventor: Lombro James Ristas, Windsor, CT (US)

( * ) Notice: Subject to any disclaimer, the term of this patent is extended or adjusted under 35 U.S.C. 154(b) by 0 days.

(21) Appl. No.: 16/697,315

(22) Filed: Nov. 27, 2019

(65) Prior Publication Data
US 2020/0179755 A1 Jun. 11, 2020

Related U.S. Application Data

(60) Provisional application No. 62/831,850, filed on Apr. 10, 2019, provisional application No. 62/775,486, filed on Dec. 5, 2018.

(51) Int. Cl.
*A63B 24/00* (2006.01)

(52) U.S. Cl.
CPC ...... *A63B 24/0021* (2013.01); *A63B 24/0087* (2013.01); *A63B 2024/0025* (2013.01); *A63B 2024/0028* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,538,910 A | * | 1/1951 | Miller ............... | F16M 11/425 348/157 |
| 2,605,557 A | * | 8/1952 | Van Deventer .... | G09B 19/0015 434/250 |
| 4,627,620 A | * | 12/1986 | Yang ................. | A63B 69/0028 273/446 |
| 4,645,458 A | * | 2/1987 | Williams ........... | A63B 69/0053 273/446 |
| 4,702,475 A | * | 10/1987 | Elstein ............... | A63B 69/0053 273/445 |
| 4,834,375 A | * | 5/1989 | Elstein ............... | A63B 24/00 273/446 |
| 5,342,041 A | * | 8/1994 | Agulnek ............ | A63B 24/0003 473/2 |
| 5,365,427 A | * | 11/1994 | Soignet ............. | A63B 24/0021 340/323 R |

(Continued)

FOREIGN PATENT DOCUMENTS

RU 2395322 7/2010

OTHER PUBLICATIONS

"Youth Basketball Drills & Sample Practice Plans," published Oct. 31, 2015 at source: https:https://ymcanwnc.org/wp-content/uploads/2015/10/Youth-Basketball-Drills-and-Practice-Plans.pdf (Year: 2015).*

(Continued)

*Primary Examiner* — Steven J Hylinski (57) ABSTRACT

A system and method for projecting a collimated beam of light from a light source to form an illuminated spot on a play surface, where an athlete is positioned adjacent to the illuminated spot. The light source is controlled with logic stored in a training pattern database, whereby the illuminated spot follows a predetermined training pattern on the play surface, prompting the athlete to move on the play surface in a movement pattern corresponding to the training pattern of the spot on the play surface.

8 Claims, 5 Drawing Sheets

(56) References Cited

U.S. PATENT DOCUMENTS

| | | | | |
|---|---|---|---|---|
| 5,683,302 A | * | 11/1997 | Harrell | A63D 5/04 473/58 |
| 6,308,565 B1 | * | 10/2001 | French | A63B 24/0003 73/379.04 |
| 6,701,872 B1 | * | 3/2004 | Allen | A01K 15/025 119/707 |
| 6,769,992 B1 | * | 8/2004 | Domulevicz | A63D 15/006 473/2 |
| 7,219,438 B2 | * | 5/2007 | Amron | G01C 15/004 33/289 |
| 7,625,314 B2 | | 12/2009 | Ungari et al. | |
| 7,834,846 B1 | * | 11/2010 | Bell | H04N 5/2256 345/156 |
| 7,864,168 B2 | * | 1/2011 | French | A63F 13/10 345/204 |
| 7,878,945 B2 | * | 2/2011 | Ungari | A63B 69/0053 482/1 |
| 8,292,733 B2 | * | 10/2012 | Crawford | A63D 15/20 463/31 |
| 8,300,042 B2 | * | 10/2012 | Bell | H04N 5/2353 345/418 |
| 8,616,971 B2 | * | 12/2013 | Lundback | A63D 15/20 463/31 |
| 9,039,012 B2 | | 5/2015 | O'Sullivan | |
| 9,084,712 B2 | * | 7/2015 | Roerdink | A61H 3/00 |
| 9,210,401 B2 | * | 12/2015 | Wilson | G16H 20/30 |
| 9,283,429 B2 | * | 3/2016 | Aragones | A63B 24/00 |
| 9,465,484 B1 | * | 10/2016 | Kamarshi | G06F 3/0425 |
| 9,759,738 B2 | | 9/2017 | Oleson et al. | |
| 9,962,570 B2 | * | 5/2018 | Dallmann | A63B 71/0622 |
| 10,122,976 B2 | * | 11/2018 | Fujiune | H04N 9/3194 |
| 10,482,778 B2 | * | 11/2019 | Yoo | F21S 4/22 |
| 2004/0102247 A1 | * | 5/2004 | Smoot | G02B 26/0816 463/36 |
| 2004/0183775 A1 | * | 9/2004 | Bell | H04N 7/183 345/156 |
| 2008/0191864 A1 | * | 8/2008 | Wolfson | G06F 3/04815 340/524 |
| 2010/0041517 A1 | * | 2/2010 | Ungari | A63B 69/345 482/8 |
| 2012/0029666 A1 | * | 2/2012 | Crowley | G06Q 10/06393 700/91 |
| 2013/0187553 A1 | * | 7/2013 | Cessna | H05B 47/155 315/161 |
| 2014/0327610 A1 | * | 11/2014 | Athavale | H04N 5/7475 345/156 |
| 2016/0188123 A1 | * | 6/2016 | Fujiune | G06F 3/005 345/156 |
| 2017/0259144 A1 | | 9/2017 | Eddie | |

OTHER PUBLICATIONS

"Can You Believe It: Lasers In Soccer?" Published Apr. 15, 2018.

* cited by examiner

| DRILL # | SUPPORT POSITION | START SPOT | PATTERN/ SEQUENCE | SPEED L/I/H | INTERVAL DELAY (SECONDS) | SAME (S) ALTRNT (A) RANDOM (R) | NUMBER OF CYCLES |
|---|---|---|---|---|---|---|---|
| 1 | S1 | 310 | P1 | L | MANUAL | S | MANUAL |
| 2 | S1 | 310 | P1 | I | 5 | S | 10 |
| 3 | S2 | 312 | P1 | I | 5 | S | 10 |
| 4 | S2 | 312 | P1, P2 | I | 10 | A | 10 |
| 5 | S2 | 312 | P1, P2 | H | 10 | A | 10 |
| 6 | S2 | 312 | P1, P2 | I | 10 | R | 5 |
| 7 | S3 | 314 | P3 | L | 10 | S | 5 |
| 8 | S3 | 314 | P3 | I | 10 | S | 10 |
| 9 | S3 | 314 | P3 | H | 10 | S | 10 |
| AD HOC | S2 | 312 | AD HOC | L | 10 | S | 10 |

FIG. 5

PROGRAMMED CONTROL OF ATHLETIC TRAINING DRILLS

BACKGROUND

The present invention relates to the training of athletes in sports that require rapid and precise movement on a play surface such as a basketball court or a football field.

As one example, basketball players must develop rapid footwork for both offensive and defensive skills. Especially on defense, slow reaction time or slow footwork in maintaining proper position relative to an offensive player driving to the basket, often results in a foul as well as a score.

As another example, football pass receivers devote much practice time running precise pass routes that not only follow a specific pattern on the ground but must also be timed to arrive at a specific point at a specific time after the ball is snapped.

SUMMARY

The present invention is directed to a system and method whereby the skill of an athlete can be improved by following a spot of light that moves along the play surface at a variable speed and variable direction as specified by a selected training program.

In a general sense, the system and method can be understood as positioning a light source in relation to a play surface, and projecting a collimated beam of light from the light source to form an illuminated spot on the play surface. An athlete is positioned adjacent to the illuminated spot. The beam is moved commensurate with logic stored in a training pattern database, whereby the illuminated spot moves to follow a predetermined training pattern on the play surface, thereby prompting the athlete to move on the play surface in a movement pattern corresponding to the training pattern of the spot on the play surface.

In one preferred implementation, a beam is projected onto a basketball court, forming a spot that is programmed to move in a preferably non-linear pattern corresponding to an offensive player driving to the basket, such that the athlete must maintain a proper defensive position ahead of the moving spot. This is especially effective in training to prevent an offensive player from driving the baseline to the basket.

In another preferred implementation, the programmed motion of the spot can trace out a football receiver's pass route and a defensive back can be trained to improve speed and agility in maintaining a good defensive position relative to the spot. Alternatively, the motion of the spot can define the pass route to be followed by a trainee pass receiver. By repetitively following the spot, the athlete learns how the route should be run.

In yet another preferred implementation, a football pass receiver wears a marker that is coupled to a remote motion sensor, and a beam is projected onto the field to form a spot that is programmed to precisely follow the path and timing of a particular pass route. A motion sensor is responsive to the time-dependent motion of the body marker. A processor compares the motion pattern of the athlete with the training pattern and generates a comparison output.

The training pattern database preferably includes a plurality of predetermined training pattern data sets. The trainer selects one of the training sets for the light source and spot to follow the training pattern on the play surface that corresponds to the selected training set. The light source articulates in three dimensions at a variable speed such that the spot moves along the play surface at a variable speed and variable direction as specified by the selected training program.

The programmed training pattern can be a stored data set supplied by the system vendor, or the end user can manually teach and store a pattern logic. Preferably, the user can optionally control the beam on a one-time, ad-hoc basis to emphasize a unique pattern.

The light box or hardware can be stationary with the 3D motion of the projection specified and controlled by a remote, and especially portable, operator interface. In a permanent practice facility where, for example, basketball teams will be coached year after year, a prescribed linear or rectilinear displacement of an overhead light box in rafters or the like, can be coordinated with 2D or 3D motion of the projection lens. This facilities rapid and precise beam projection anywhere on the entire court.

The system and method can be used in other ways for basketball and football, and in a variety of ways for other sports played on a flat, solid surface.

BRIEF DESCRIPTION OF THE DRAWING

Representative features and embodiments of the invention will be described in greater detail below, with reference to the accompanying drawing, in which.

DETAILED DESCRIPTION

Figure 1:
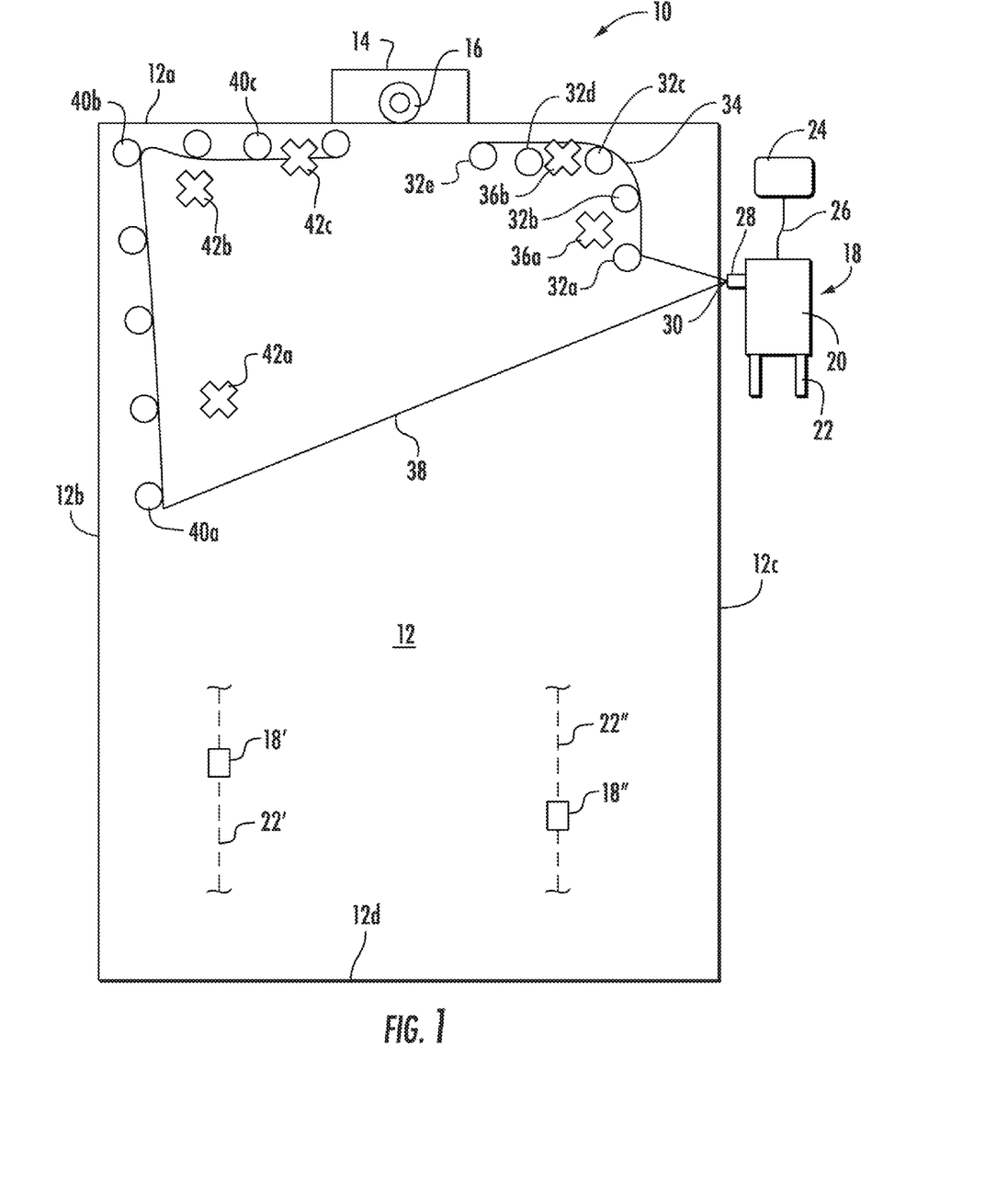
FIG. 1 shows an embodiment of the invention as implemented on a basketball court.
Figure 2:
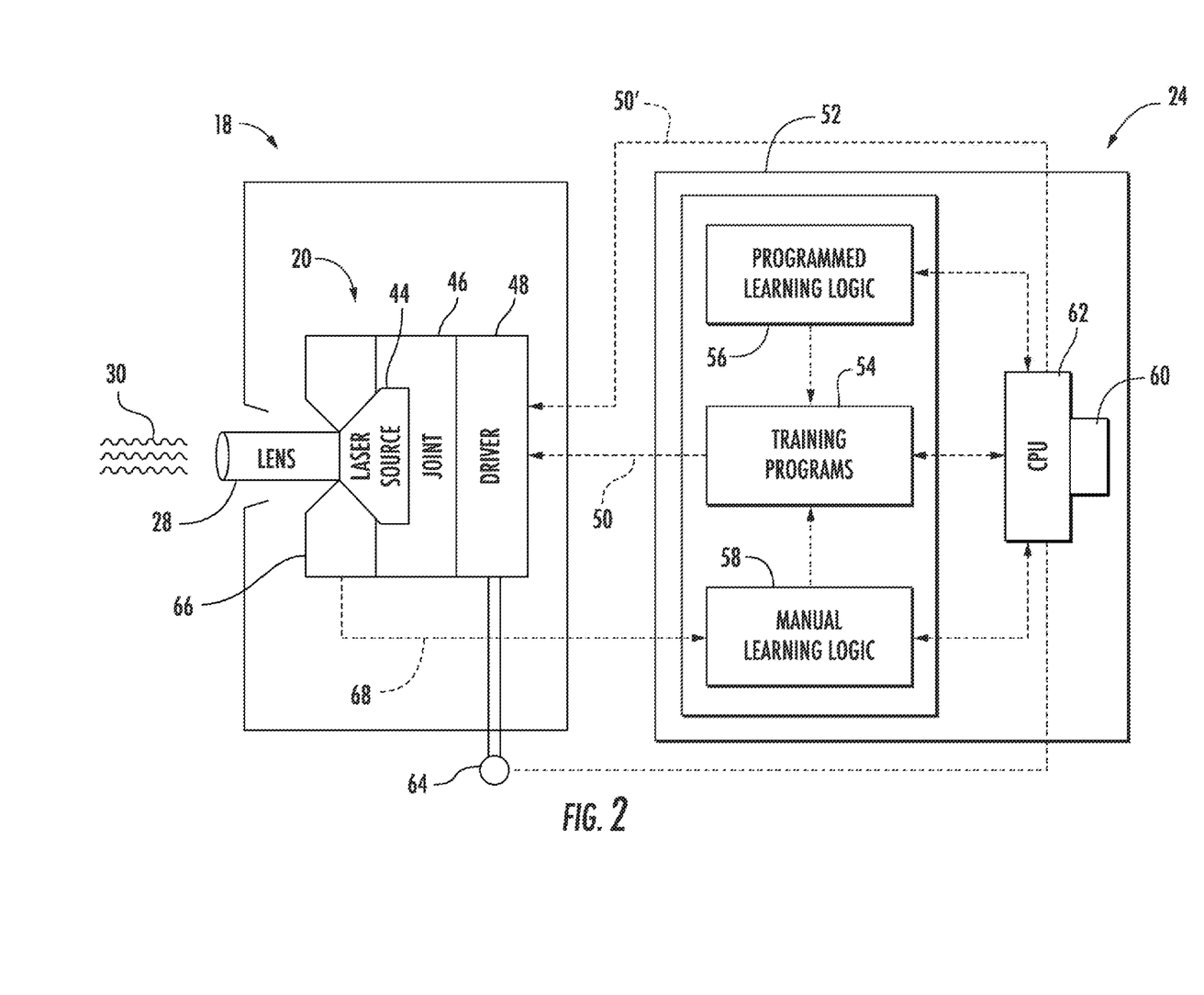
FIG. 2 is a schematic of the main components of the inventive system.

FIG. 1 shows an exemplary configuration 10 on a basketball court 12 having base lines and side lines 12a-d, with only one backboard 14 and basket 16 shown, on baseline 12a. A light box 18 with internals 20 shown schematically in FIG. 2, is supported 22 along sideline 12c but could be positioned anywhere in relation to the court 12. A trainer's interface 24 is shown with a communication path 26 to the light box. This path 26 could be hard wired to or physically integrated with the light box 18, or coupled via a spaced or remote connection, such as with a Bluetooth® interface.

The light box includes a lens system 28 including housing, through which a beam of light 30 is projected onto the play surface 12. In one training drill moving spot 32 is produced by beam 34, whereas in another drill spot 40 is produced by beam 38. The lens 28 can be variably articulated in three dimensions in response to a control signal such that the projected beam of light 34 or 38 moves non-linearly and produces corresponding non-linearly moving spots 32, 40, which are represented with a respective series of circles 32a-d and 40a-c in FIG. 1 but in practice would move continuously along the entire paths represented by lines 34 and 38.

For a drill to protect baseline 12a, the lens would produce stationary or starting spot 32a and the athlete would be positioned in a defensive stance X shown at 36a. Preferably without warning, the lens 28 would move the spot through the sequence 32b-e while the athlete tries to maintain his or her position with hips ahead of the spot. In particular, when the spot is moving on the curved path toward a clear lane to the baseline for the imaginary offensive player to shoot at spot 32e, the athlete tries to beat the spot 32c to the lane, thereby blocking the path by arriving at defensive position X at 36b while the spot is at 32c. Spot 32 can be programmed to move along the play surface at a variable speed and variable direction as specified by a selected training program stored internally. This programming can be fine-tuned to represent the speed and footwork of a particular opponent's player, who may have a history on video of effectiveness from particular starting positions on the court.

A similar drill is shown with beam 38 and moving spot 40, which is initially farther from the basket at 40a where the defender would be spaced somewhat farther as represented by the X at 42a. Since the imaginary offensive player represented at 40a could dribble either left or right, the athlete at 42a does not know which programmed pattern the trainer is about to initiate (i.e., left or right), so the trainee must be very focused. The pattern represented by spots 40a-40c goes to the trainees right and, by analogy to the previously described drill, the trainees must maintain good defensive position with ultimate blocking at 42c of a drive path to the basket.

In this way the trainer can objectively assess the reaction time, footwork, agility and current capabilities of each player on the team (especially new players). By customizing the spot patterns with respect to path on the court and speed of movement, the coach or trainer can tailor the patterns to provide continuous improvement for each individual player. Once all the desired programmed patterns have been stored, the coach and an assistant coach can determine which pattern will be drilled on which practice days for each player. In this way, the assistant can drill one player while the coach works with the rest of the team at the other end of the court or the drill can be set up in a smaller, auxiliary gym, without a basket.

It should be appreciated that the programmed patterns would typically be referenced or calibrated with respect to a reference light box mounting position relative to the court. Each pattern need not be referenced to the same reference position, and a given pattern could be started at other than its referenced starting position. With the light positioned as shown in FIG. 1, neither the beam trace 34 nor the spots 32 should project onto the trainee. In fact, if the trainee interrupts the beam or spot, the trainees would have likely fouled the represented offensive player.

With the light box at the position shown in FIG. 1 and the associated beam 38 and spot pattern 40, it is possible the beam would be intermittently interrupted by the trainee moving between 42a and 42c. However, this would be substantially equivalent to using a discontinuous or pulsed light source, which is within the scope of the present invention. The trainee would still see a spot movement pattern sufficient to prompt an appropriate defensive response. Alternatively, the light box could be relocated to a different reference position.

Rather than featuring one portable light box as needed, the system could have one or more light boxes 18', 18" permanently mounted overhead such that the light beams project more vertically. Programming and control can easily be achieved remotely. All patterns could be referenced to the same fixed position of the light box, and set-up time and beam interruption would be minimized. Alternatively, the light source could be mounted on an overhead track 22', 22" such as shown in dashed lines, for selective repositioning to preestablished reference points over different areas of the floor before projecting a pattern, or the mounting fixture of the source on the track could be driven along the track while the source projects a controllable 2D or 3D beam.

With reference to both FIGS. 1 and 2, the interface 24 is operatively associated with the internals 20 of light box 18. The interface can be considered a combination of stored program and data 52, such as stored training programs 54, stored program learning logic 56, and manual learning logic 58. A terminal 60 with input/output and associated processor 62 are digitally connected to the stored programs, logic and data 52. As used herein, "controller" can be considered the functional operation of the interface 24. This does not preclude some or all of the programs and data 52 and possibly the interface 24, being integrated with the light box. 18.

The light box includes a light source 44, a lens system 28 through which a beam of light 30 from the source is projected onto the play surface and an integrated or distinct joint 46 by which the lens can be variably articulated in two or three dimensions. An integrated or distinct driver 48 articulates the joint in response to a control signal 50 from the controller. The controller 24 includes a plurality of digitally stored training programs 54, with each training program specifying a different sequence of control signals to the driver for defining a respective three-dimensional articulation pattern for the lens. The trainer uses the interface 24 to select a particular training program; whereby the controller articulates the lens 28 such that the projected beam of light produces the spots 32a-e, 40a-c that move along the play surface at a variable speed and variable direction as specified by the selected training program.

The interface 24 preferably includes an analogue to digital converter and a digital to analogue converter for creating a custom or specifically tailored training program 54 using either programmed learning logic 56, or manual learning logic 58, that define a desired time-dependent articulation pattern in 54. At 60, the trainer selects which of the stored training programs 54 will executed, and when.

The lens driver 48 can operate in three modes. The normal mode is responsive to the control signal 50 from the training program module 54. Another mode is directly responsive to either a control signal 50' from the keyboard 60 or manual control from a joystick 64 or the like, to produce an unprogrammed, one-time, ad-hoc projection pattern, instead of executing a stored training program 54. In a third mode, lens driver 48 is again responsive to either a digital control signal 50' from keyboard or manual control from joystick 64, to establish a movement pattern that defines the manual learning logic 58. This mode is implemented in combination with a lens position sensor 66, and a position generator for delivering a position input signal 68 to the manual learning module 58, commensurate with the driven position of the lens 28.

Whether supplied as a pre-packaged set of programmed patterns by the system provider or programmed by the user in a series of logic instructions (at 56), or programmed by the joystick or equivalent (at 58), the plurality of programs can be stored in one data file indicated at 54 which informs the driver control signal 50.

Mono beam single color laser systems are commercially available that can project a bright spot on the ground at a distance of at least 30 meters and can be programmed/ trained by the purchaser to store a variety of 3-D motion patterns. Alternatively, a simple, consumer-grade mono beam laser can be mounted in a multi-axis fixture or joint (as represented at 46 in FIG. 2), with programmed 3-D articulation of the fixture to implement a variety of standard motion patterns that would be included with the system as sold to the end user. The programming algorithm could also be supplied to the end user for customization of programs by the end user.

Multi-axis motion of a laser can be programmed by analogy to other industrial control systems. Industrial laser projectors are often used as optical guidance systems. They enable working without templates in many manufacturing processes by showing directly on the workpiece how material needs to be positioned or mounted, whereby the worker is led to perform manual or semiautomatic productional processes visually by the laser. These systems can be optimized for fast and stable projection with high repetition rate (50 Hz) and 2D and 3D projection over a wide optical angle (80 deg.×80 deg.) The present invention leads or guides an athlete to perform a desired operation (e.g., defensive footwork) on a workpiece (e.g., basketball court).

Figure 3:
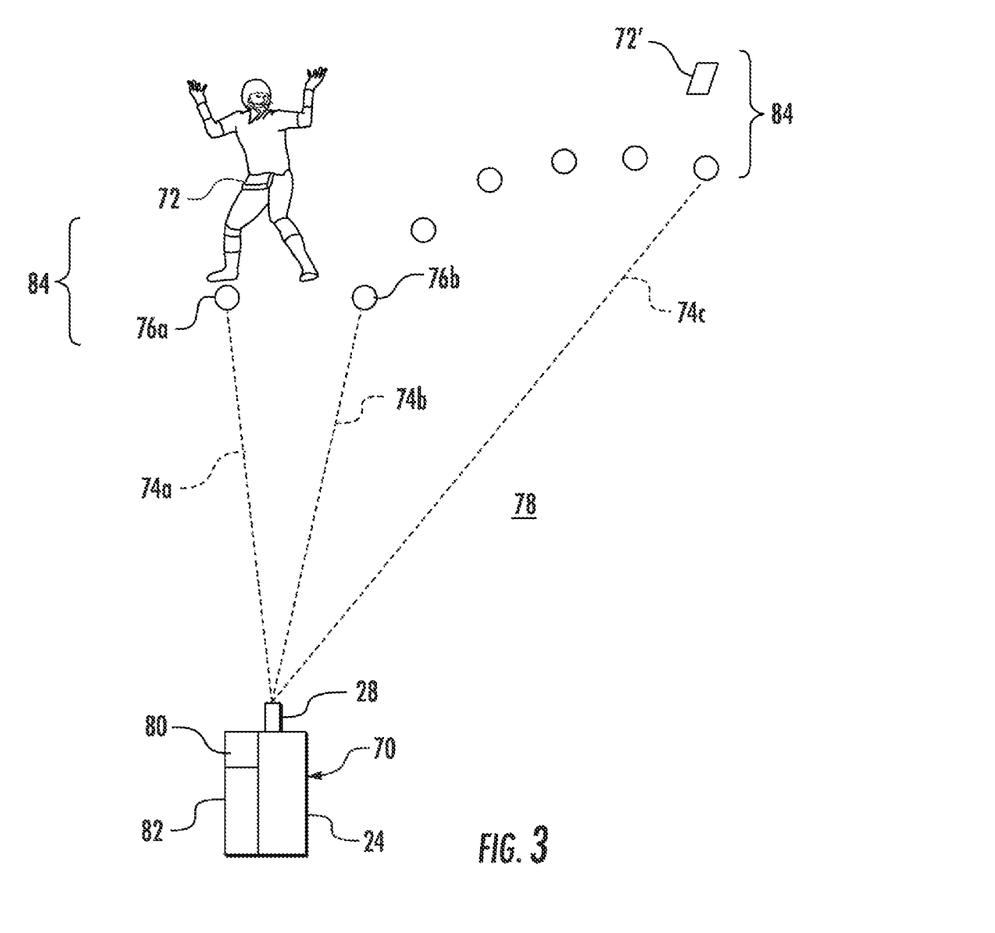
FIG. 3 shows an embodiment of the invention as implemented on a football field.

FIG. 3 represents use of a more comprehensive embodiment, for training football pass receivers. The system as described with respect to FIG. 1 can be used for this purpose, if only to indicate to the trainee the correct pattern and timing of the route. If the performance is to be objectively evaluated, supplemental features can be provided.

In this regard, the system 70 is augmented relative to the system 10 as described with respect to FIG. 2 for use in conjunction with a body marker 72 securable to the athlete whereby a time-dependent motion pattern of the body marker is commensurate with the motion of the athlete when the athlete tries to follow the spot 76a,b,c of the projected beam 74a,b,c of light that moves along the play surface 78 at a variable speed and variable direction as specified by the selected training program in the interface. A motion sensor 80 at a reference position relative to the light box is responsive to the time-dependent motion of the body marker 72. The processor in interface 24 or a different processor 82 with associated logic compares the motion pattern of the athlete against the training pattern specified by the interface and generates a comparison output. Since the marker 72 is on, e.g., the hip of the trainee, the comparison includes an offset 84 between the spot 76c of the beam of the training pattern leading the athlete and the marker 72' the spot as the athlete follows the spot.

A major advantage of the system applicable to any field of athletics is not only precise repetition of a given pattern, but also that the execution speeds of the patterns can be precisely varied from day to day, thereby increasing the challenge to and thus proficiency of the athlete. Another advantage associated with the manual learning logic 60, is that a learning pattern can be traced out very slowly and precisely with the joystick 64, then later executed in real time at any desired speed during training of the athlete. In a further option, the controller can include a program to display the play surface and an image of the selected training pattern on the interface 60 and enable the trainer to re-shape the pattern on the display with a corresponding modification and storing of the re-shaped training program pattern. This is analogous to how lines drawn with the "shapes" insert in a word processing program, can be stretched or rotated.

Although the system and method are especially adapted for improving the rapid directional transition and speed of so-called "footwork", the predetermined pattern of a moving spot can be useful in, for example, track and field. The spot can be programmed to trace out the target speed of a sprinter, hurdler, relay segment, or even a lap on an oval track.

Figure 4:
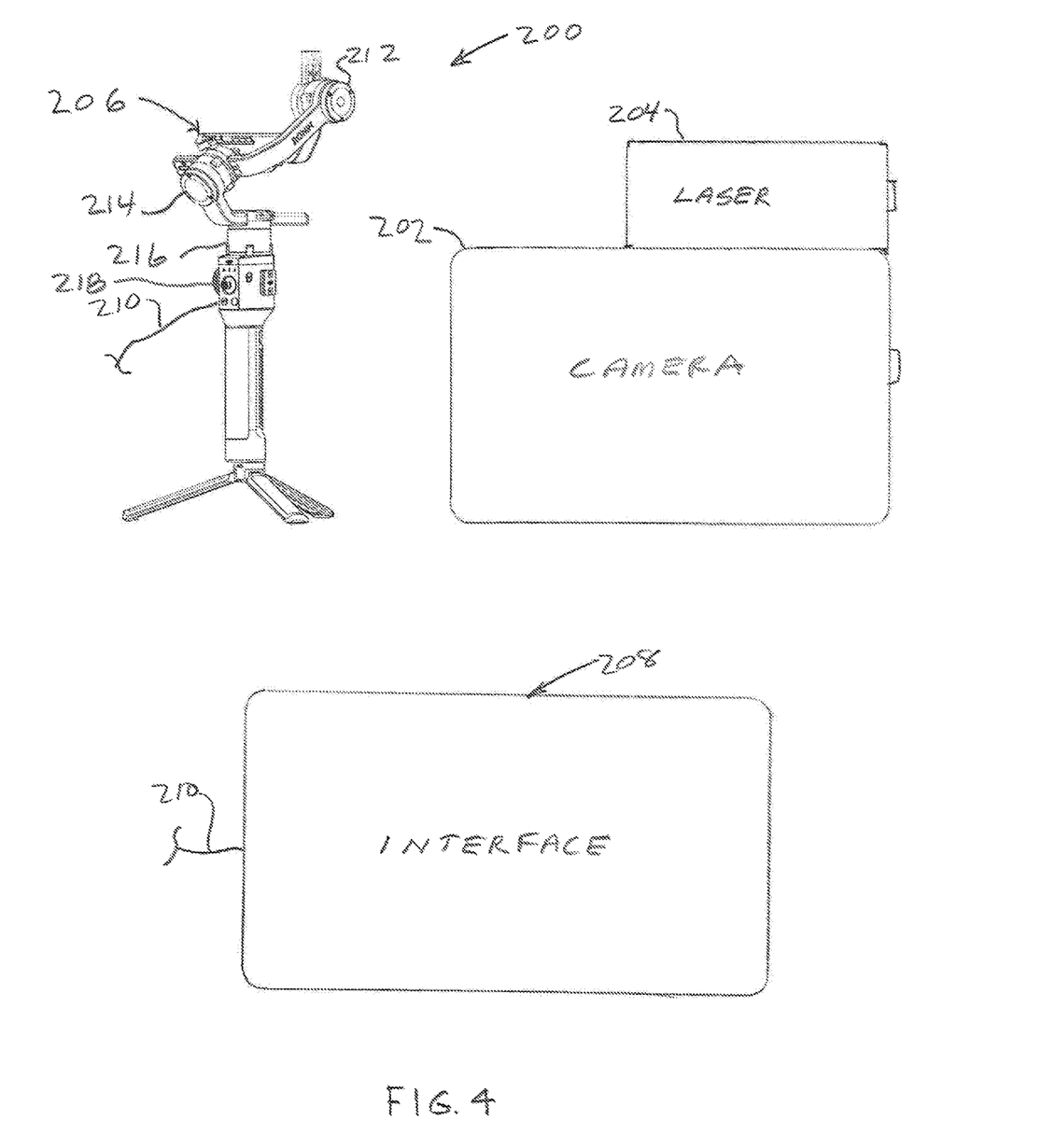
FIG. 4 show one embodiment of a controlled laser and video camera combination on a tripod support.

FIG. 4 illustrates further adaptations of the system and method. In this embodiment 200, a video camera 202 and laser 204 combination are connected to the support 206 (not to scale), either (i) stationary with a wide field of view that covers the entire trace of the moving spot and associated following movement of the player, or (ii) a shown, coupled to the laser 204 for synchronous movement with a narrower field of view that follows the moving spot and player's moving feet.

A fully functional system can be built around a video camera tracking platform such as the DJI Ronin-S available from the Chinese company DJI, but adapted to articulate a laser instead of or in combination with a video camera. This platform is a three-axis gimbal camera support with controller, mountable on a tripod or slider. For the present invention, the controller can be embodied in the more comprehensive hand-held unit 208 operated by the trainer, connected either by cable 210 or wireless. Motors are provided for tilt 212, roll 214, and pan 216. A joystick 218 is also present.

In the Tracking mode, a plurality of waypoints can be defined, thereby programming a corresponding pattern for the laser spot to trace out. The travel speed between successive waypoints can be specified, thereby modelling any combination of the movement attributes of acceleration, full stride, pivoting, deceleration, and stopping.

Off the shelf, this Ronin-S platform is programmable and controllable via wireless connection to a smartphone or tablet for implementing the built-in features. An alternative platform is the DJI OSMO Pocket, in which the built-in video camera can be replaced by a laser. The motion is programmable to the same extent as the Ronin-S.

In a simple implementation, the waypoint and timing features can be configured by the system supplier for standard, sport-specific patterns. To achieve greater flexibility, a somewhat sophisticated end-user coaching staff can teach the system additional patterns using the waypoint and timing features. In a more comprehensive system, the supplier can develop custom add-on or modified controller software, especially the user interface, display, and navigation, consistent with the present disclosure, so the platform with controller can be adapted to store many sports-specific trace patterns, each executable at any of a variety of selectable speeds, starting at any of a variety of selectable locations of the laser relative to the play surface. For a given sport, the stored data that defines a trace pattern can reproduce the movement pattern of a known high-performance athlete, derived from the programmer's analysis of images of that athlete during actual competition.

The system and method are especially adapted for coaching one player in a repetitive series of a particular one or multiple patterns, thereby intensively challenging and improving the footwork of that player. However, the system is adaptable to group training. The recovery rate for repeating the execution of a selected pattern is only a matter of seconds. Thus, once the laser is set up at a particular location relative to the play surface, the initial spot can consistently establish a reference marker at a point on the play surface for aligning a plurality of players in single file. The first player follows a first pattern of spot tracing, while the second player in line steps up to the initial position relative to the reference point, ready for recovery of the spot and execution of a second pattern that is the same as or different from the first pattern.

In this way, each one of a full team of, for example, twelve basketball players can be efficiently run through multiple iterations of the same or variable patterns in an overall time of only five to ten minutes taken out of a one to two-hour practice session. In another example, baseball players can line up behind home plate and sequentially follow a trace that defines the ideal track for running out an extra-base hit. Most players run in a wide arc around first base toward second base, but a series of short straight path segments is more efficient. The laser trace can train the player to run straight toward first base, approach the base with a slight outward move, then turn sharply inward so the outside foot pushes off the inside corner of the base, thereby redirecting the player into a straight path toward second base.

Figure 5:
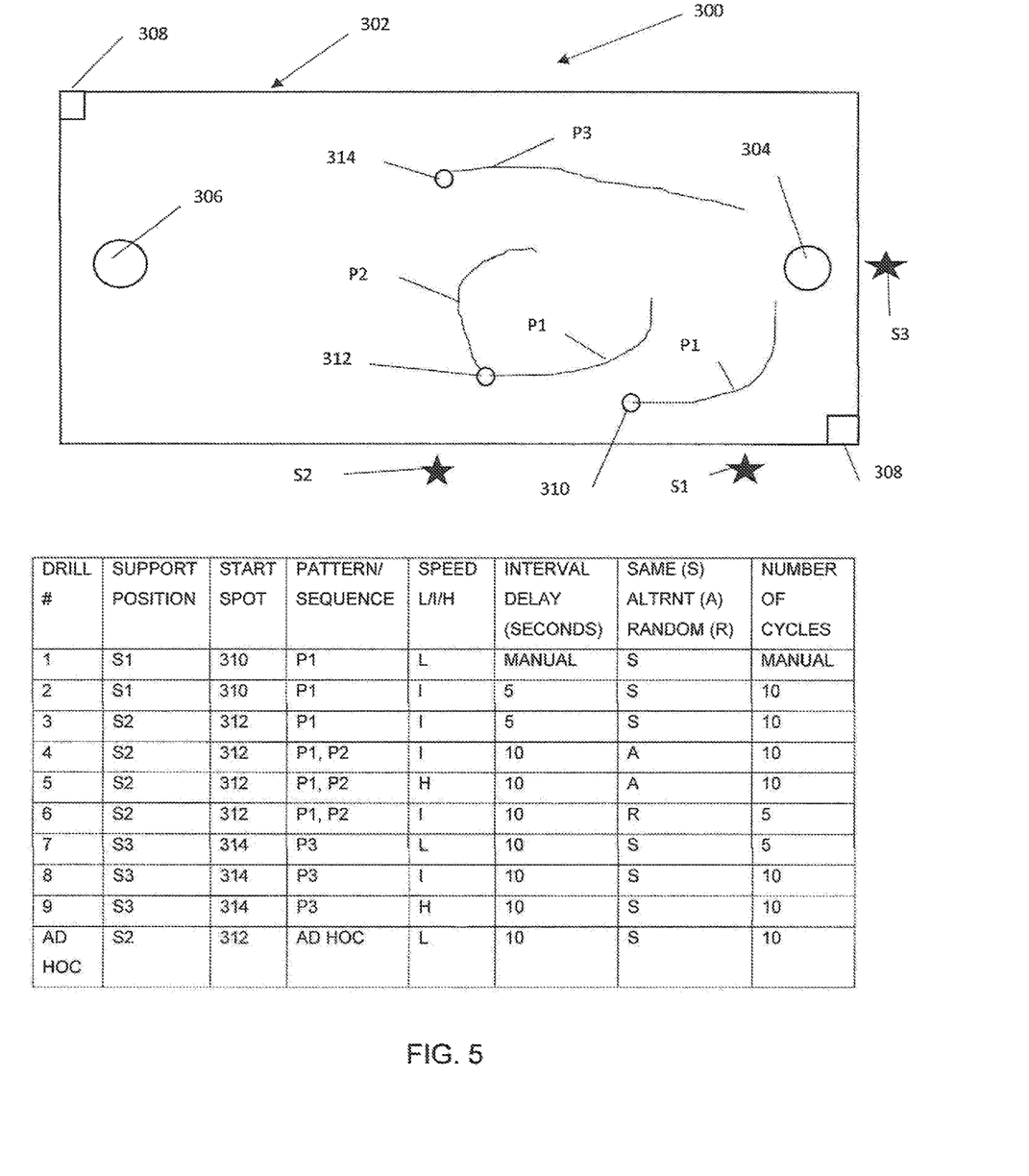
FIG. 5 shows a representative interface that displays stylized images of a basketball court and several possible training patterns, with a touchpad that enables the coach to select various starting points and patterns.

In a fully automated system, the interface can be programmed for user navigation on a display screen 300 such as shown in FIG. 5. The display has an upper portion that represents a play surface 302, such as a basketballer court with baskets 304 and 306. If desired for calibration purposes, marks at the opposite corners 308 and 310 of the court can be provided to help define a plurality of, for example, three support stations S1, S2, S3 at, for example, midway between the center line, the centerline, and under the basket, respectively. Patterns P1, P2, and P3 are represented. The shape of a particular pattern such as P1 is independent of its starting position. Pattern P1 is shown as starting at spot position 310 or 312. Pattern P2 can also start at spot position 312. Pattern P3 starts at spot position 314. The starting spot can be selected by coordinates or by touching the screen.

In a typical use, only one starting spot position would be selected and shown on the display portion 302, but several are shown in FIG. 5 for illustrative purposes in conjunction with the pattern selection interface 316 in the lower portion of the display screen 300. For simple Drill #1 the position of the support is selected as S1 to project the starting spot at 310, for motorized tracing out spot pattern P1 at low speed L. The same trace is repeated at the trainer's discretion under manual control M, so there is no selectable number of cycles. Instead, the drill trace is repeated as desired by touching the MANUAL field again.

Drill #2 is selectable for the same support position S1 and starting spot 310, but traced out at intermediate speed I with each same trace S for Pattern P1 automatically initiated at five second intervals, for a total of ten cycles.

Drill #3 is selectable for support at position S2 and starting spot position 312, for also tracing pattern P1 at intermediate speed at five second intervals for ten cycles.

Drill #4 is selectable for support at position S2 and starting spot position 312, for tracing sequential patterns P1 and P2 at intermediate speed and ten second intervals, alternating A for ten cycles.

Drill #5 is selectable for support at position S2 and starting spot position 312, for tracing sequential patterns P1 and P2 at high speed H and ten second intervals, alternating A for ten cycles.

Drill #6 is selectable for support at position S2 and starting spot position 312, for randomly R tracing patterns P1 and P2 at intermediate speed at ten second intervals, for five cycles.

Drill #7 is selectable for support at position S3 and starting spot position 314, for tracing the same pattern P3 at low speed at ten second intervals for five cycles.

Drill #8 is selectable for support at position S3 and starting spot position 314, for tracing the same pattern P3 at intermediate speed at ten second intervals for ten cycles.

Drill #9 is selectable for support at position S3 and starting spot position 314, for tracing the same pattern P3 at high speed H at ten second intervals for ten cycles.

Any number of such drills can be programmed and stored for selection by scrolling and then firmly touching the selected DRILL #field. The default values appear in the same row, but the user can sequence through the available options in any given column (such as speed options L/I/H). A particular combination could be as a default for a particular drill, or the same combination could be achieved by sequencing options from a selected drill. For example, Drill #8 could be replicated by starting with Drill #7 and incrementing the speed from L to I.

The last row enables the user to generate an ad-hoc drill by touching the AD HOC field, selecting a support position such as S2 and start spot such as 312, then manually moving the laser spot along a desired path on the play surface (as also represented in the display screen 302) to an end point, whereupon the AD HOC field is pushed gain to set the AD HOC pattern. The values in the other fields of that row can then be selected, such as L, 10, S, and 10.

Another option is to provide a dual beam whereby the trace is projected at one color (e.g., green) and at the end of the trace a different color is projected (e.g., red). The different color can represent the offensive player stopping to take a basketball shot or football catch, with the coach instructing on the ideal defensive reaction. This adds one more prompt to which the athlete must react in a way specified by the coaches. If the athlete is not in the ideal defensive position at the moment the color changes, the coach can instruct on how to recover at least partially, without incurring a penalty. The dual beam can be incorporated into a single multi-color laser with color-change switch or two synchronized lasers with controlled timing.

By analogy to both defensive and offensive training described with respect to FIG. 3 for football, the present invention can be used for basketball to trace out a repeatable path (such as P3 in FIG. 5) for an offensive player to follow from a particular starting position 314 to a shooting or passing position. Two beams can be controlled, to coordinate the movement of a first offensive player from, for example, position 314 along a predetermined path P3, with the movement along path P1 of a second offensive player who starts at position 310 to receives a pass from the first player for a layup basket. Another option (not shown) is to control two beams for coordinating defensive rotation whereby a second defensive player closer to the basket backs up a primary defensive player who first encounters an offensive player who is driving toward the basket.

In yet another mode, for simply improving lateral or oblique quickness, a beam can be projected in front of a player and the beam moved laterally side to side at a predetermined or increasing rate between preselected end points, without necessarily simulating an offensive player's movement on a play surface for a particular sport. This can be further modified by controlling the beam to project an internally or externally curved path on the play surface, returning each cycle to the starting point.

It should be appreciated that the function or step of specifying a different sequence of control signals to the driver for defining a respective three-dimensional articulation pattern for the lens, includes the equivalent of providing, e.g., a fixed laser with associated mirror as an element of the lens system and three-dimensional control of a driver for the mirror. Also, although a continuous beam is preferred, whereby one spot appears to move continuously along the play surface, the system and method could be implemented by a stroboscopic beam with which a series of closely spaced, individual spots defines the training pattern.

The invention claimed is:
1. A system for training athletes for sports that are played on a play surface, comprising:
a light box;

a support for positioning the light box in relation to a play surface;

a controller operatively associated with the light box;

wherein the light box includes a light source, a lens system through which a collimated beam of light from the light source is projected onto the play surface, a joint by which the lens system can be variably articulated, and a driver for articulating the joint in response to a control signal from the controller;

wherein the controller includes a plurality of digitally stored training programs, each training program specifying a different sequence of control signals to the driver for defining a respective three-dimensional articulation pattern for the lens system, and an input device by which a trainer selects a particular training program;

whereby the controller articulates the lens system such that the projected beam of light includes a spot visible on the play surface and that moves along the play surface at a variable speed and variable direction as specified by the selected training program; and wherein the input device includes a user-responsive selection screen configured to program the controller to execute any one of a plurality of drills, each drill defining multiple characteristics including a start spot on the play surface, a particular pattern for the spot to trace on the play surface from the start spot, a speed at which the spot traces the pattern, a number of cycles that the pattern will be traced, and a delay interval between the start of each cycle.

2. The system of claim 1, wherein the drill characteristics include at least two patterns that start from the same start spot; and whether the at least two patterns are executed sequentially, alternatively or randomly.

3. A system for training athletes for sports that are played on a play surface, comprising:

a light box;

a support for positioning the light box in relation to a play surface;

a controller operatively associated with the light box;

wherein the light box includes a light source, a lens system through which a collimated beam of light from the light source is projected onto the play surface, a joint by which the lens system can be variably articulated, and a driver for articulating the joint in response to a control signal from the controller;

wherein the controller includes a plurality of digitally stored training programs, each training program specifying a different sequence of control signals to the driver for defining a respective three-dimensional articulation pattern for the lens system, and an input device by which a trainer selects a particular training program;

whereby the controller articulates the lens system such that the projected beam of light includes a spot visible on the play surface and that moves along the play surface at a variable speed and variable direction as specified by the selected training program; and wherein the controller comprises a trainer input module for creating a custom training program that defines a desired time-dependent articulation pattern, and a digital processor, a manually operated lens system manipulator, a lens position sensor, and a position generator for delivering a position input signal to the controller commensurate with the manipulated driven position of the lens system, whereby in a pattern learning mode of operation the processor converts the manually driven pattern into a digitally stored custom training program.

4. A method for training athletes for sports that are played on a play surface, comprising:

positioning a light source in relation to a play surface;

projecting a collimated beam of light from the light source to form an illuminated spot on the play surface;

positioning an athlete adjacent to the illuminated spot;

moving the beam commensurate with logic stored in a training pattern database, whereby the illuminated spot moves to follow a predetermined training pattern on the play surface;

prompting the athlete to move on the play surface in a movement pattern corresponding to the training pattern of the spot on the play surface;

positioning another light source in relation to said play surface;

projecting a collimated beam of light from the other light source to form another illuminated spot on the play surface;

positioning another athlete adjacent to the other illuminated spot;

controlling the other light source with logic stored in the training pattern database, whereby the other illuminated spot follows another predetermined training pattern on the play surface; and prompting the other athlete to move on the play surface in another movement pattern corresponding to the training pattern of the other spot on the play surface;

whereby the athletes simultaneously follow coordinated movement patterns on the play surface.

5. A method for basketball defensive training of at least one player, comprising:

positioning a laser system for articulated movement to project a spot of light on a basketball court, the court having spaced apart parallel sidelines, at least one base line that intersects the sidelines, and a basket midway along the baseline;

providing stored instructions and data accessible by a coach on an interface controller that is in functional communication with the laser system, for selecting a training drill from a plurality of training drills that causes the spot of light to follow a selected one of a plurality of predetermined opponent movement patterns corresponding to the selected drill;

projecting the spot of light at a starting location on the court adjacent the at least one player and spaced from the sideline and the baseline and moving the spot in a curved path toward the basket, that simulates the speed and path of movement of an offensive opponent dribbling a ball toward the basket; and whereby the at least one player is prompted to follow the spot to maintain defensive positioning relative to the spot.

6. The method of claim 5, for training a plurality of players, including:

the spot of light at the starting location prompting the plurality of players to align behind the spot;

prompting a first of the aligned players to move on the court in a first movement pattern corresponding to a first training pattern of the spot on the court;

after the first player has completed the first movement pattern, prompting a second of the aligned players to move on the court in a second movement pattern corresponding to a second training pattern of the spot on the court; and repeating the prompting until all players have been prompted to follow respective movement patterns to maintain defensive positioning relative to the spot.

7. The method of claim 5, wherein the spot increases in speed as it follows the trace.

8. The method of claim 5, wherein through the interface controller, the coach also selects two patterns that start from the same start spot; such that one pattern curves toward the basket along the baseline and the other pattern curves toward the basket away from the baseline; and whether the two patterns are executed alternatively or randomly.

\* \* \* \* \*